(12) United States Patent
Fujiwara et al.

(10) Patent No.: US 8,658,815 B2
(45) Date of Patent: Feb. 25, 2014

(54) METHOD FOR PRODUCING RUTHENIUM COMPLEX

(75) Inventors: Takahiro Fujiwara, Tokyo (JP); Hideki Nara, Tokyo (JP)

(73) Assignee: Takasago International Corporation, Tokyo (JP)

( * ) Notice: Subject to any disclaimer, the term of this patent is extended or adjusted under 35 U.S.C. 154(b) by 133 days.

(21) Appl. No.: 13/138,709

(22) PCT Filed: Mar. 18, 2010

(86) PCT No.: PCT/JP2010/055296
§ 371 (c)(1),
(2), (4) Date: Sep. 21, 2011

(87) PCT Pub. No.: WO2010/113773
PCT Pub. Date: Oct. 7, 2010

(65) Prior Publication Data
US 2012/0016148 A1    Jan. 19, 2012

(30) Foreign Application Priority Data
Apr. 2, 2009   (JP) ................................. 2009-090290

(51) Int. Cl.
*C07F 15/00* (2006.01)
(52) U.S. Cl.
USPC ........................................................ 556/136
(58) Field of Classification Search
USPC ........................................................ 556/136
See application file for complete search history.

(56) References Cited

FOREIGN PATENT DOCUMENTS

| CN | 101555260 A | 10/2009 |
| JP | 11-322649 A | 11/1999 |
| JP | 2001-104795 A | 4/2001 |
| JP | 2006-076935 A | 3/2006 |
| WO | WO 02/40494 A1 | 5/2002 |

OTHER PUBLICATIONS

Jensen, S. et al. "Facile preparation of n6-p-cymene ruthenium diphosphine complexes. Crystal structure of [(n6-p-cymene)Ru(dp-pf)Cl]PF6," J. Organomet. Chem. (1998) 556: 151-158.*

Jafarpour et al., "(p-cymene)RuLCl2 (L=1,3-Bis(2,4,6-trimethylphenyl)imidazol-2-ylidene and 1,3-Bis(2,6-diisopropylphenyl)imidazol-2-ylidene) and Related Complexes as Ring Closing Metathesis Catalysts," Organometallics 1999, 18:3760-3763.

Mashima et al., "Cationic BINAP-RU(II) Halide Complexes: Highly Efficient Catalysts for Stereoselective Asymmetric Hydrogenation of α- and β-Funcationalized Ketones," J. Org. Chem., 1994, 59:3064-3076.

Suravajjala et al., "Bis(arene) complexes of $Ru^{II}$. Synthesis, crystal structure and electrochemical behavior of $[bis(\eta^6\text{-}p\text{-}isopropyltoluene)Ru][BF_4]_2$," Journal of Organometallic Chemistry, 1993, 461:201-205.

Jikken Kagaku Koza (Courses in Experimental Chemistry), The Fifth Series of Experimental Chemistry, 21:221-224, with 2 page partial translation, (2004).

\* cited by examiner

*Primary Examiner* — Porfirio Nazario Gonzalez
(74) *Attorney, Agent, or Firm* — Foley & Lardner LLP

(57) ABSTRACT

The present invention provides a method for inexpensively producing di-μ-chloro-bis[chloro($\eta^6$-1-isopropyl-4-methylbenzene)ruthenium (II)] complex used as a catalyst raw material for a hydrogenation or metathesis polymerization reaction at a high yield. In the present invention, the above-described problem can be solved by reacting ruthenium chloride or a hydrate thereof with γ-terpinene in a solvent. In particular, by using an alcohol having a boiling point of 100° C. or higher as a solvent, the yield of the above-described complex can be increased.

4 Claims, No Drawings

METHOD FOR PRODUCING RUTHENIUM COMPLEX

CROSS-REFERENCE TO RELATED APPLICATIONS

This application is a National Stage application of PCT/JP2010/055296, filed Mar. 18, 2010, which claims priority from Japanese application JP 2009-090290, filed Apr. 2, 2009.

TECHNICAL FIELD

The present invention relates to a method for producing a ruthenium complex to be used as a catalyst raw material for a hydrogenation or metathesis reaction.

BACKGROUND ART

The complex represented by the following formula (1), i.e., di-μchloro-bis [chloro($\eta^6$-1-isopropyl-4-methylbenzene)ruthenium (II)] complex (hereinafter sometimes referred to as "Ru-CPC complex") is used as a catalyst raw material for a hydrogenation reduction reaction, metathesis reaction or the like (see: Journal of Organic Chemistry, Vol. 59, 3064 (1994) (Non-patent Literature 1); Organometallics, Vol. 18, 3760 (1999) (Non-patent Literature 2); etc.).

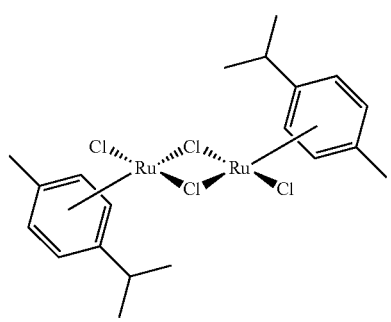

(1)

As methods for producing a Ru-CPC complex, the following two methods are known. One is a method in which 10 ml of α-phellandrene is reacted with 2.0 g of ruthenium chloride hydrate under the reflux of 100 ml of ethanol for 4 hours, and the reaction mixture is cooled, followed by separating the obtained crystal by filtration ("Jikken Kagaku Koza (Courses in Experimental Chemistry)", Vol. 21, 5th edition, page 221 (Non-patent Literature 3)). Another is a method in which 200 ml of ethanol, 45 ml of α-terpinene and 22 ml of water are added to 10 g of ruthenium chloride hydrate and the mixture is refluxed for 4 hours, and after that, most of ethanol is removed by distillation, followed by separating the obtained crystal by filtration (Japanese Laid-Open Patent Publication No. 11-322649 (Patent Literature 1)).

α-phellandrene, which is a conventional raw material, is most efficiently and most inexpensively produced by steam distillation from leaves of eucalyptus (Eucalyptus dives Schuer Type). However, the supply is easily influenced by weather, etc. Thus, in terms of stable supply, α-phellandrene has a big problem. Regarding α-terpinene, it can be generally obtained by extraction from a natural product or chemical synthesis. However, because of extraction from a natural product, in terms of stable supply, α-terpinene has a problem.

Further, in the case of chemical synthesis thereof, α-terpinene having a purity of 90% or more is not commercially available.
Therefore, there is a problem that the production cost to obtain a high-purity Ru-CPC complex is high.

CITATION LIST

Patent Literature

Patent Literature 1: Japanese Laid-Open Patent Publication No. 11-322649

Non-patent Literature

Non-patent Literature 1: Journal of Organic Chemistry, Vol. 59, 3064 (1994)
Non-patent Literature 2: Organometallics, Vol. 18, 3760 (1999)
Non-patent Literature 3: "Jikken Kagaku Koza (Courses in Experimental Chemistry)", Vol. 21, 5th edition, page 221

SUMMARY OF INVENTION

Technical Problem

Under the above-described circumstances, it is desired that a technique for complex production to enable a high-purity Ru-CPC complex to be efficiently produced from a stably-supplied raw material without influences of weather, etc. is provided.

Solution to Problem

The present inventors diligently made researches to solve the above-described problems, and found that a Ru-CPC complex can be inexpensively produced at a high yield by reacting ruthenium chloride or a hydrate thereof with γ-terpinene in a solvent. Thus, the present invention was achieved.
Specifically, the present invention provides a method for producing a ruthenium complex as described below:
[1] A method for producing a ruthenium complex represented by the following formula (1):

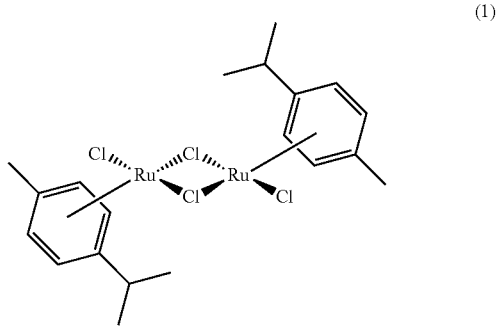

(1)

wherein ruthenium chloride or a hydrate thereof is reacted with γ-terpinene in a solvent.
[2] The method according to item [1], wherein the solvent includes alcohol.
[3] The method according to item [1] or [2,] wherein the solvent includes alcohol having a boiling point of 100 to 300° C.

Advantageous Effects of Invention

According to the method of the present invention, not by extraction from a natural product but by using a high-purity raw material which can be stably provided industrially, a Ru-CPC complex can be inexpensively produced at a high yield.

DESCRIPTION OF EMBODIMENTS

Hereinafter, the present invention will be described in detail.

In the present invention, ruthenium chloride or a hydrate thereof is reacted with γ-terpinene in a solvent.

Ruthenium chloride (meaning "ruthenium (III) chloride" in this specification) is a typical ruthenium compound, and ruthenium chloride itself is used as a raw material for plating or an electrode material. In general, ruthenium chloride is commercially available in the form of hydrate (ruthenium (III) chloride -n-hydrate (n is a number of 1 to 4)). In the present invention, it is also preferred that ruthenium chloride is used in the form of hydrate.

γ-terpinene in a small quantity is commercially available as a reagent. Further, γ-terpinene is also available on industrial scale. Commercially available γ-terpinene usually has a purity of 95% or more, and therefore, it can be directly used in a reaction without purification. For example, γ-terpinene can be obtained from Millennium Inorganic Chemicals, Destilerias Munoz Galvez S.A., Takasago International Chemicals (Europe) S.A., Destilaciones Bordas Chinchurreta, SA, etc. Several methods for producing γ-terpinene are publicly known. Examples thereof include: an isomerization treatment of turpentine oil under acidic conditions; a treatment of α-pinene with concentrated sulfuric acid; a dehydration treatment of piperitol; and an isomerization treatment of α-phellandrene or limonene under acidic conditions (for example, see: U.S. Pat. No. 2,799,717 (1957); Liebigs Annalen der Chemie, Vol. 2,234 (1986); and Journal of the American Oil Chemists' Society, Vol. 82, 531 (2005)).

In the present invention, ruthenium chloride or a hydrate thereof is preferably used in an equimolar amount of γ-terpinene, but from the viewpoint of easiness of purification, etc., γ-terpinene is preferably used in a slight molar excess. For example, the amount of γ-terpinene is preferably 1 to 20 times, more preferably 2 to 10 times, and even more preferably 3 to 6 times the amount of ruthenium chloride or a hydrate thereof (molar ratio).

The solvent to be used in a reaction is not particularly limited as long as both ruthenium chloride or a hydrate thereof and γ-terpinene can be solved. Since a desired reaction rate can be obtained, alcohol is preferably used. Specific examples thereof include aliphatic alcohols, aromatic alcohols, diols and derivatives thereof.

Examples of aliphatic alcohols include n-butanol, 2-butanol, n-pentanol, 2-pentanol, 3-pentanol, 3-methyl-1-butanol, cyclopentanol, n-hexanol, 2-hexanol, 3-hexanol, cyclohexanol, n-heptanol, 2-heptanol, 3-heptanol, cycloheptanol, n-octanol, 2-octanol, 3-octanol, 4-octanol, and cyclooctanol.

Examples of aromatic alcohols include phenol, benzyl alcohol, 1-phenylethanol, 2-phenylethanol, o-cresol, m-cresol, p-cresol, 2-methylbenzyl alcohol, 3-methylbenzyl alcohol, and 4-methylbenzyl alcohol.

Examples of diols and derivatives thereof include ethylene glycol, 1,2-propanediol, 1,3-propanediol, 1,2-butanediol, 1,3-butanediol, 1,4-butanediol, 2-methoxyethanol, 2-ethoxyethanol, 2-isopropoxyethanol, ethylene glycol n-butyl ether, ethylene glycol iso-butyl ether, ethylene glycol n-hexyl ether, 3-methoxy-1-butanol, and 3-methoxy-3-methyl-1-butanol.

Among the above-described substances, since the Ru-CPC complex can be obtained at a higher yield, an alcohol having a boiling point of 100° C. or higher is preferably used. The boiling point of alcohol is more preferably 120° C. or higher, and particularly preferably 125° C. or higher. The upper limit of the boiling point of alcohol is not particularly limited, but is preferably 300° C. or lower, more preferably 250° C. or lower, and particularly preferably 210° C. or lower because of easiness of operation.

Examples of particularly preferred alcohol solvents include cyclohexanol, benzyl alcohol, n-pentanol, n-hexanol, n-heptanol, 2-methoxyethanol, and 2-ethoxyethanol.

In the present invention, the solvents may be used solely or in combination. By combining 2 or more types of solvents, the boiling point of the solvent can be adjusted to a desired range, and when a reaction is performed under the reflux, a reaction temperature can be adjusted. For example, a small amount of water may be mixed with alcohol for use.

The amount of the solvent to be used is not particularly limited as long as it is an amount with which ruthenium chloride or a hydrate thereof is dissolved at a reaction temperature. For example, it is 2 to 50 times the volume of ruthenium chloride or a hydrate thereof (i.e., 2 to 50 mL of solvent per 1 g of ruthenium chloride or a hydrate thereof; the same applies to the following), preferably 2 to 30 times the volume thereof, and more preferably 5 to 20 times the volume thereof.

In the present invention, a reaction is preferably performed under the reflux. The reaction pressure is not particularly limited, but is preferably ordinary pressure because of easiness of operation.

The reaction temperature varies depending on the type of solvent to be used, but is preferably 100° C. or higher, and more preferably 120° C. or higher in terms of the reaction efficiency. Further, because of easiness of operation, the reaction temperature is preferably 200° C. or lower, and more preferably 160° C. or lower.

The reaction time varies depending on the reaction scale, the type of solvent and the molar ratio between ruthenium chloride and γ-terpinene, but usually, it is preferably 1 to 20 hours, and more preferably 2 to 8 hours.

EXAMPLES

Hereinafter, the present invention will be described in more detail based on the working examples and comparative examples, but the present invention is not limited to the working examples. Note that the following apparatuses were used in the measurement of physical properties, etc. in the working examples below: NMR: Mercury plus 300, Varian Technologies Japan Limited $^1$H-NMR; 300.07 MHz
$^{31}$P-NMR; 121.48 MHz Gas chromatography (GC): 6890-type column, Agilent Technologies

Example 1

Production of Ru-CPC Complex Using Cyclohexanol (Boiling Point: 161° C.)

100 ml of cyclohexanol, 10 ml of water and 15.6 ml of γ-terpinene were added to 5.0 g of ruthenium chloride hydrate (n=about 2.6), and the mixture was stirred and heated on oil bath at 120° C. for 4 hours. After that, the solvent was distilled away under reduced pressure.

20 ml of diisopropyl ether was added to the obtained concentrate at room temperature to precipitate a product, and it was stirred overnight.

Next day, after cooled on ice bath and stirred at 5° C. or lower for 1 hour, the precipitated crystal was separated by filtration, and the obtained crystal was washed twice with 10 ml of cooled diisopropyl ether. The crystal was dried under reduced pressure, thereby obtaining 5.70 g of red Ru-CPC complex. The yield of the Ru-CPC complex was 97%.

The data of $^1$1-H-NMR measurement is shown below.
$^1$H-NMR (CDCl$_3$, δ): 1.27 (6H, d, J=6.9 Hz), 2.15 (3H, s), 2.92 (1H, m, 6.9 Hz), 5.33 (2H, d, 6.0 Hz), 5.47 (2H, d, 6.0 Hz)

Example 2

Production of Ru-CPC Complex Using Benzyl Alcohol (Boiling Point: 205° C.)

2.5 ml of benzyl alcohol, 0.25 ml of water and 1.6 ml of γ-terpinene were added to 0.50 g of ruthenium chloride hydrate (n=about 2.6), and the mixture was stirred and heated on oil bath at 120° C. for 4 hours. After that, the solvent was distilled away under reduced pressure.

15 ml of diisopropyl ether was added to the obtained concentrate at room temperature to precipitate a product, and it was stirred overnight.

Next day, after cooled on ice bath and stirred at 5° C. or lower for 1 hour, the precipitated crystal was separated by filtration, and the obtained crystal was washed twice with 2 ml of cooled diisopropyl ether. The crystal was dried under reduced pressure, thereby obtaining 0.55 g of red Ru-CPC complex. The yield of the Ru-CPC complex was 93%.

Example 3

Production of Ru-CPC Complex Using N-Pentanol (Boiling Point: 137.5° C.)

10 ml of n-pentanol, 1.0 ml of water and 1.6 ml of γ-terpinene were added to 0.50 g of ruthenium chloride hydrate (n=about 2.6), and the mixture was stirred and heated on oil bath at 120° C. for 4 hours. After that, the solvent was distilled away under reduced pressure.

10 ml of diisopropyl ether was added to the obtained concentrate at room temperature to precipitate a product, and it was stirred overnight.

Next day, after cooled on ice bath and stirred at 5° C. or lower for 1 hour, the precipitated crystal was separated by filtration, and the obtained crystal was washed twice with 2 ml of cooled diisopropyl ether. The crystal was dried under reduced pressure, thereby obtaining 0.56 g of red Ru-CPC complex. The yield of the Ru-CPC complex was 95%.

Example 4

Production of Ru-CPC Complex Using 2-Methoxyethanol (Boiling Point: 125° C.)

10 ml of 2-methoxyethanol, 1.0 ml of water and 1.6 ml of γ-terpinene were added to 0.50 g of ruthenium chloride hydrate (n=about 2.6), and the mixture was stirred and heated on oil bath at 120° C. for 4 hours. After that, the solvent was distilled away under reduced pressure.

10 ml of diisopropyl ether was added to the obtained concentrate at room temperature to precipitate a product, and it was stirred overnight.

Next day, after cooled on ice bath and stirred at 5° C. or lower for 1 hour, the precipitated crystal was separated by filtration, and the obtained crystal was washed twice with 2 ml of cooled diisopropyl ether. The crystal was dried under reduced pressure, thereby obtaining 0.58 g of red Ru-CPC complex. The yield of the Ru-CPC complex was 98%.

Example 5

Production of Ru-CPC Complex Using N-Butanol (Boiling Point: 118° C.)

10 ml of n-butanol, 1 ml of water and 1.6 ml of γ-terpinene were added to 0.50 g of ruthenium chloride hydrate (n=about 2.6), and the mixture was stirred and heated on oil bath at 120° C. for 4 hours. After that, the solvent was distilled away under reduced pressure.

20 ml of chloroform was added to the obtained concentrate at room temperature to separate insolubles by filtration. The filtrate was concentrated, and 10 ml of diisopropyl ether was added thereto to precipitate a product. It was stirred overnight.

Next day, after cooled on ice bath and stirred at 5° C. or lower for 1 hour, the precipitated crystal was separated by filtration, and the obtained crystal was washed twice with 2 ml of cooled diisopropyl ether. The crystal was dried under reduced pressure, thereby obtaining 0.44 g of red Ru-CPC complex. The yield of the Ru-CPC complex was 75%.

Example 6

Production of Ru-CPC Complex Using Ethanol (Boiling Point: 78.3° C.)

20 ml of ethanol, 2.2 ml of water and 3.1 ml of γ-terpinene were added to 1.00 g of ruthenium chloride hydrate (n=about 2.6), and the mixture was stirred and heated on oil bath at 120° C. for 4 hours. After that, the solvent was distilled away under reduced pressure.

20 ml of chloroform was added to the obtained concentrate to separate insolubles by filtration. The filtrate was concentrated, and 20 ml of diisopropyl ether was added thereto to precipitate a product. It was stirred overnight.

Next day, after cooled on ice bath and stirred at 5° C. or lower for 1 hour, the precipitated crystal was separated by filtration, and the obtained crystal was washed twice with 4 ml of cooled diisopropyl ether. The crystal was dried under reduced pressure, thereby obtaining 0.585 g of red Ru-CPC complex. The yield of the Ru-CPC complex was 50%.

INDUSTRIAL APPLICABILITY

According to the method of the present invention, a Ru-CPC complex can be inexpensively produced at a high yield. The Ru-CPC complex obtained using the method of the present invention is suitably used as a catalyst raw material for a hydrogenation or metathesis reaction.

The invention claimed is:

1. A method for producing a ruthenium complex represented by the following formula (1):

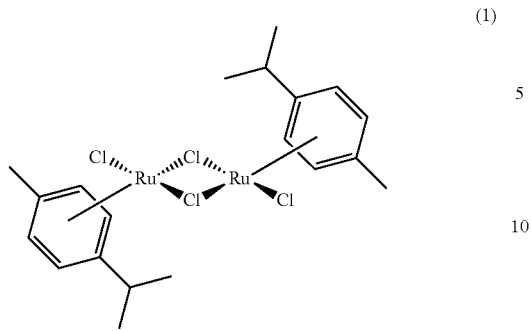 (1)

wherein ruthenium chloride or a hydrate thereof is reacted with γ-terpinene in a solvent, and the solvent includes an alcohol having a boiling point of 100 to 300° C.

2. The method according to claim 1, wherein the alcohol is selected from the group consisting of cyclohexanol, benzyl alcohol, n-pentanol, n-hexanol, n-heptanol, 2-methoxyethanol, 2-ethoxyethanol and any combination thereof.

3. The method according to claim 1, wherein the reaction is performed at a temperature between 100 and 200° C.

4. The method according to claim 1, wherein the reaction is performed at a temperature between 120 and 200° C.

* * * * *